United States Patent
Lutz

(10) Patent No.: US 11,071,310 B1
(45) Date of Patent: Jul. 27, 2021

(54) ORAL THERAPY ARTICLE, AND METHODS OF USING SAME

(71) Applicant: Natalie Marie Lutz, Hockessin, DE (US)

(72) Inventor: Natalie Marie Lutz, Hockessin, DE (US)

( * ) Notice: Subject to any disclaimer, the term of this patent is extended or adjusted under 35 U.S.C. 154(b) by 0 days.

(21) Appl. No.: 15/980,700

(22) Filed: May 15, 2018

Related U.S. Application Data

(63) Continuation of application No. 14/973,678, filed on Dec. 17, 2015, now abandoned.

(60) Provisional application No. 62/092,935, filed on Dec. 17, 2014.

(51) Int. Cl.
*A23G 4/06* (2006.01)
*A61F 5/58* (2006.01)

(52) U.S. Cl.
CPC ............. *A23G 4/066* (2013.01); *A61F 5/58* (2013.01); *A23V 2002/00* (2013.01)

(58) Field of Classification Search
CPC ... A61F 5/58; A23G 4/00–205; A61K 9/0058; A61Q 11/00–02
See application file for complete search history.

(56) References Cited

U.S. PATENT DOCUMENTS

| | | | | |
|---|---|---|---|---|
| 2002/0012633 A1* | 1/2002 | Gmunder | ................. | A23G 4/06 424/48 |
| 2007/0032554 A1* | 2/2007 | Kelsey | .................... | A61K 31/00 514/651 |
| 2019/0060228 A1* | 2/2019 | Bruun | .................... | A61K 47/24 |

\* cited by examiner

*Primary Examiner* — Thaddeus B Cox
(74) *Attorney, Agent, or Firm* — Ramberg IP, LLC; Jeffrey R. Ramberg

(57) ABSTRACT

A collection of therapies that are useful in a speech pathology setting, the common denominator of the therapies is that they each make use of chewing gum. Chewing gum administered to a patient can be used to treat swallowing disorders and oral motor impairments. In a major aspect of the invention, a series or kit of chewing gums of varying hardness can be used to treat mastication disorders. The gum exercise program will use the varying gum hardnesses as exercises for the muscles of the mouth, mastication, oral motor, sensory/stimulation, and swallowing therapeutic interventions. The instant therapies are more functional than existing dysphagia and oral motor interventions because they are similar to masticating real food by eliciting saliva production and taste buds from the gustatory response of the lemon and sour flavors. In addition, for sensory/stimulation exercises, the varying degrees of gum hardness, along with the lemon and other flavors, provide sensory feedback.

20 Claims, No Drawings

ORAL THERAPY ARTICLE, AND METHODS OF USING SAME

CROSS-REFERENCE TO RELATED APPLICATION

This patent document is a Continuation of U.S. patent application Ser. No. 14/973,678, filed on Dec. 17, 2015, now abandoned, which claims the benefit of U.S. Provisional Patent Application Ser. No. 62/092,935, filed on Dec. 17, 2014, both in the name of Natalie Marie Lutz. The entire contents of these commonly owned patent applications are expressly incorporated by reference herein.

STATEMENT REGARDING FEDERALLY SPONSORED RESEARCH

None.

BACKGROUND OF THE INVENTION

1. Field of the Invention

The instant invention relates to therapies for oral pathologies. The invention more specifically relates to an article that a speech language pathologist can use to help patients who have difficulty chewing, swallowing, and/or oral motor impairments, and regimens or procedures that the speech pathologist can follow using the instant article.

2. Discussion of Related Art

Patients with dysphagia, feeding, oral motor, and sensory disorders have difficulty chewing and reduced sensation, and there are few exercises that are functional or similar to masticating food that activates neuro pathways in speech pathology and related qualified therapeutic disciplines.

Traditional dysphagia therapy for oral pathologies such as reduced mastication consists of patients masticating food to improve oral dysphagia. However, food will break down and does not allow for continuous exercise of the masseter muscles. The instant invention allows for continuous mastication that is similar to a food bolus, but will not break down during mastication.

In addition, speech pathologists typically will use plastic chewy tubes to address oral motor impairments and dysphagia/feeding disorders. A "chewy tube" (Chewy Tube Company, South Portland, Me.) typically is made from plastic, and features a biting portion that is placed inside the patient's mouth and which portion the patient bites down on, and a handle portion connected to the biting portion, and which handle portion remains outside of the patient's mouth, and permits the therapist to insert and withdraw the biting portion relative to the patient's mouth. They may have little impact on neuro pathways because this handle anchors down the chewy tube, reducing the natural movement of a free form bolus. Chewy tubes are not very functional in dysphagia therapy because they are not similar to food mastication. Furthermore, chewy tubes are typically used in the pediatric population and may have a juvenile appearance in the adult/geriatric population.

The instant invention addresses the shortcomings of the known art.

SUMMARY OF THE INVENTION

What is provided in accordance with the instant invention is a collection of therapies that are useful in a speech pathology setting, the common denominator of the therapies is that they each make use of chewing gum. For example, chewing gum administered to a patient can be used to treat dysphagia and/or oral motor impairments. In a major aspect of the invention, a series or kit of chewing gums of varying hardness can be used to treat mastication disorders.

DETAILED DESCRIPTION OF ASPECTS OF THE INVENTION

In accordance with a major aspect of the invention, what is provided is a series, set or kit of chewing gums of varying hardness (e.g., varying density or chewing resistance) that are useful in a speech pathology setting; thus, this aspect of the invention also includes methods of using these chewing gums. A speech pathologist or other qualified therapist (sometimes referred to simply as "therapist") will first need to assess the patient's oral motor deficits or sensory deficits and determine which gum hardness or item (one through five) will be most appropriate for maximizing the exercises. After the patient appears to be making improvements, the speech pathologist/or other qualified therapist may increase the resistance to a higher hardness gum such as level one, or reduce the resistance to a lower hardness gum such as level five. The gums may also be flavored with a lemon or sour flavor to elicit a gustatory response. In this way, the patient can practice swallowing skills. This product of this aspect of the instant invention is different from chewing conventional gum because it is formulated to exercise the jaw and masseter muscles by changing the degrees of hardness of the gum.

The gum exercise product would allow patients to chew an item of varying degrees of resistance, starting with the easiest level then working up to a more difficult to masticate gum texture for speech pathology exercises to improve oral motor function/mastication in impaired individuals. Optionally, the gum exercise product may be provided with a lemon/sour flavor that would elicit a gustatory response to improve sensation.

The gum exercise program will use the varying gum hardnesses as exercises for the muscles of the mouth. The instant gum exercise program is more functional and similar to masticating real food, for example, the gustatory response of the lemon and sour flavors, that is, stimulating the taste buds and eliciting saliva production.

Relationship Between the Components

It is envisioned that the instant gum exercise product will feature about five gums, that is, chewing gums of about five different hardnesses.

Items (or levels) one through five will best be utilized initiating the oral exercise gum program with number five first and using the other gum hardnesses to advance to a more dense (harder) level of gum resistance such as, number one. However, they can be used in any order as seen fit by the speech pathologist or other qualified therapist to target the patient's appropriate resistance level to maximize the exercise.

How the Invention Works

A speech pathologist/other qualified therapist could use each component such as levels one through five individually to exercise the oral mechanism, or use the gums in a succession starting with the lowest resistance gum such as the level five gum, then increase to level four, then to level three, next level two and as the patient improves the speech pathologist or other qualified therapist would introduce the level one gum, if it is appropriate. It is up to the discretion of the speech pathologist/other qualified therapist to determine what level of gum hardness is most appropriate at that time for the patient to maximize the results of the exercise.

A speech pathologist/other qualified therapist will first need to assess the patient's oral motor deficits or sensory deficits, and determine which gum hardness or item (one through five) will be most appropriate for maximizing the exercises. After the patient appears to be making improvements, the speech pathologist/or other qualified therapist may increase the resistance to a higher hardness gum such as level one. A speech pathologist/other qualified therapist will need to monitor the patient for safety concerns with the gum as well.

Alternatively, there is at least one disorder where a lower hardness chewing gum is indicated as the patient's oral skill improves. Specifically, where the speed of chewing is the disorder, beginning with a harder chewing gum may be indicated, as the harder gums are chewed more slowly. As the patient demonstrates proficiency with slow chewing, a softer chewing gum may be administered, along with instructions to try to chew this gum faster. Sometimes, the patient does not have to be told to chew a softer gum faster; it tends to occur naturally or spontaneously.

This repeated chewing exercise is unlike anything in the field because typically chewing food is used in oral dysphagia therapy, and foods are chewed then swallowed, not allowing for prolonged chewing exercise. The therapy gum allows for various gum hardnesses to be trialed to exercise and improve muscle, oral motor strength, and mastication sequencing. The therapy gum allows for extended chewing exercise time without breakdown that occurs during food trials in traditional dysphagia/oral function therapy. If the patient demonstrates food pocketing or oral stasis, the speech pathologist could utilize the therapy gum exercises to address these oral deficits. For example, the patient could masticate the therapy gum, then lateralize the gum with their tongue from the affected side, and back and forth. Furthermore, the patient could be instructed to use a lingual sweep strategy to maneuver the gum from the affected side. In this way, the patient would be exercising and mimicking food without the breakdown that occurs with food trials and addressing the patient's deficits. The benefit of this invention allows the patient to repeatedly perform these exercises over and over again in therapy. In addition, the lemon/sour flavor is a gustatory stimulant that provides additional sensory feedback.

The Chewing Gum Exercise Kit

The major components of chewing gum are gum base, hardness modifier, and sweetener. In a production or commercial setting, typically a synthetic gum base is used. The hardness modifier can be a plasticizer (softener) such as glycerin. Hardeners such as sorbitol may be used with commercial chewing gums.

In the small scale or laboratory setting, the inventor found it easier to use natural chicle for the gum base instead of the synthetic material that chewing gum manufacturers use. Without addition of a hardening agent, a hardness of 58 was produced on the Shore OO scale, and this was deemed sufficiently hard that no additional hardener was deemed necessary. Conversely, glycerin did not produce as much softening effect as it does with synthetic gum base, so the inventor used coconut oil with good softening results. Other oils such as vegetable oils should also work. Chewing gums of varying softness were produced by varying the ratio of coconut oil (softener) to the chicle gum base.

The gums having varying hardness may be color-coded so that the speech pathologist can quickly and easily know the hardness of a specific gum. Color can be provided to the gum by adding food coloring during the batching process.

The gum stock or base is made more pleasant and thus more palatable, by adding some flavoring. A sweetener may be added, for example, confectioners' sugar. Other natural sugars include honey and molasses. The sweetener may be applied by coating the exterior surface of the gum with the sweetener. Particularly for those patients who are diabetic or whose glucose levels should not be changed by the therapy, the sweetener may be artificial instead of a natural substance.

The inventor has found that a chewing gum that elicits a gustatory or salivary response is often desirable and useful. A lemon or sour flavor is useful in this regard. Citric acid can be added to the gum composition to produce a lemon/sour flavor.

Citric acid is the basis of citrus fruit flavors, e.g., lemon/lime/grapefruit. It is used to create a sour flavor. Previously, it was made from lemons or limes, but a fungi was discovered that produces the same citric acid and sour taste that is more cheaply reproduced.

The traditional method for stimulating the taste buds and eliciting a gustatory response has been to administer with a cotton swab a mixture of glycerin and lemon juice/citric acid. The inventor has learned, however, that certain patients, particularly those recovering from oral cancer and perhaps undergoing radiation and/or chemotherapy, do not respond well to the lemon or sour flavor; it can be too overwhelming. The protective mucosa in their oral cavity can become damaged during the chemo/radiation process. The cancer specialists recommend not using the lemon swabs with this population. The inventor wanted to have another option for speech pathologists to use the gum with the oral/head and neck cancer population. Accordingly, for such patients, the inventor has eliminated the lemon/sour flavor. One substitute that the inventor has found for the lemon/sour flavor is peppermint. The peppermint is a strong flavor that can be used for those that have been exposed to radiation/chemo for oral/head/neck cancer. The peppermint can be used to stimulate the taste buds without being overwhelming. It is another option for those that cannot tolerate the sour bolus.

Preparation and Hardness Characterization of Chewing Gums

A series of chewing gums were prepared of different hardnesses. Each recipe yielded enough gum for a single serving to one patient. Note that three teaspoons equals the volume of one tablespoon. Natural chicle is the gum base. Coconut oil functions as a softener. Citric acid provides a lemon/sour flavor. Confectioner's sugar provides sweetness. Hardness was measured after 30 seconds of chewing using a durometer on the Shore OO scale. A total of three readings were taken on each grade of chewing gum. The flavorings did not change the hardness readings by more than a point or two.

Approximately 1 teaspoon of room temperature coconut oil was added to about 1 tablespoon of natural chicle gum base and thoroughly blended. The mixture was shaped as a square about one-half square inch in size and about one-half inch thick. To this molded shape was added 1 drop of yellow food coloring and 1 drop of citric acid. Confectioner's sugar was sprinkled over the surface to yield a yellow-colored chewing gum.

The durometer reading of this gum was 8, meaning that a very soft gum had been produced. This corresponds to the previously mentioned "Level 5" gum.

Other gums of different hardness were produced. A soft orange gum was produced by substituting orange food coloring for yellow, and by substituting one-half teaspoon of coconut oil for the one teaspoon of the yellow gum. This "Level 4" orange gum had a hardness of 19 on the Shore OO scale.

A medium hardness red gum was produced by substituting red food coloring for yellow, and by substituting one-quarter teaspoon of coconut oil for the one teaspoon of the yellow gum. This "Level 3" red gum had a hardness of 29 on the Shore OO scale.

A hard green gum was produced by substituting green food coloring for yellow, and by substituting one-eighth teaspoon of coconut oil for the one teaspoon of the yellow gum. This "Level 2" green gum had a hardness of 44 on the Shore OO scale.

A very hard blue gum was produced by substituting blue food coloring for yellow, and by eliminating the coconut oil altogether. This "Level 1" blue gum had a hardness of 58 on the Shore OO scale.

An earlier batch of chicle-based chewing gums also featured Shore OO scale hardnesses of 45, 33 and 26.

Peppermint/Sugar Version

A peppermint/sugar version of the gum is produced using the aforementioned recipe of the second paragraph of the preceding subsection, substituted with peppermint extract instead of the citric acid.

Peppermint/Sugar Free Version

A peppermint/sugar free version of the gum is produced using the aforementioned recipe bf the preceding paragraph, substituted with sugar substitute instead of sugar.

Lemon-Sour/Sugar Free Version

A Lemon-Sour/Sugar Free Version of the gum is produced using the aforementioned recipe of the second paragraph of the subsection entitled, "Preparation and hardness characterization of chewing gums", substituted with sugar substitute instead of confectioner sugar.

The inventor personally tested the Level 1 hardest chewing gum and indicated that the hardness of the chewing gum provided an exceptional muscular response of the masseter and jaw mechanisms.

Other Therapies Using Chewing Gum

In addition, to the above-described chewing therapies, the chewing gum (sometimes referred to as "therapy gum") could also be used to complete "hard swallows and dry swallows" in traditional swallowing treatment. For example, speech pathologists will sometimes train patients who need to strengthen their swallow to do saliva swallows (dry swallow) and hard swallows (a dry swallow with effort/muscle effort behind it). One problem the inventor noticed with this therapy is that patients do not constantly have saliva to swallow repeatedly quickly enough. To solve this problem, one could chew the gum to create saliva, and then remove it to swallow their saliva as a hard swallow or dry swallow. Thus, the gum is an improvement or adjunct to this therapy because it allows for increased saliva production to continuously perform the dry/effortful swallows. Another option would be, if the patient was capable, the patient could store the gum between their cheek and teeth on the side of mouth while swallowing the saliva they are continuously producing due to chewing the gum. The speech pathologist would have the patient focus on an "effortful swallow". This would allow the patient to repeatedly perform dry swallows/effortful swallows easier and more frequently than waiting to develop saliva naturally. The overall result would be increasing therapeutic repetitions and possibly increasing outcomes.

The speech pathologist will note the difference between oral stage dysphagia and pharyngeal stage, as the therapies will differ depending on the type. Oral dysphagia involves disordered deglutition of the oral phase of the swallow whereas pharyngeal dysphagia involves disordered deglutition of the pharyngeal phase of the swallow. The speech pathologist can address both; namely, by addressing the oral phase with chewing, and pharyngeal phase via swallow initiation of saliva. This provides a natural swallowing process similar to foods (chewing and swallowing) that chewy tubes and other foreign objects cannot provide. The gum follows the natural sequence of swallowing from chewing to swallow initiation (of saliva). It is intended to be used by those patients who can follow directions to not swallow the gum.

Previously, the swallowing therapy technique of choice for use with a patient that is not yet ready for food consumption (for example, a patient who is unable to have food or liquid by mouth), relied upon ice chips. Thus, the chewing gum could be used in this situation as a transition from ice chips to food. When a patient is on an oral diet and eating by mouth, typically dysphagia therapy involves trialing various food textures and hardnesses. For example, a patient may be on a pureed diet due to dysphagia. The speech pathologist traditionally would trial harder textures and solids to advance the patient's diet to a harder solid texture. There is very limited existing therapy to improve mastication repeatedly. That is why the inventor felt the gum would be beneficial. Some speech pathologists will utilize a lemon glycerin cotton swab in treatment, which involves the patient sucking on the swab and swallowing their saliva. The therapy gum would be more advantageous because it would allow for more saliva production as well as consistent mastication, and it has the lemon flavor that the cotton swab contains.

A current therapeutic treatment for dysphagia exists that involves neuromuscular electrical stimulation via electrodes. This treatment is intended to be completed while performing swallowing exercises. The therapy gum using dry/effortful swallows could be utilized during neuromuscular electrical stimulation. Ice chips, food/liquid trials are often used with hard swallows during the neuromuscular electrical stimulation. The therapy gum provides the masticatory and swallowing process involved in deglutition and it may be a safer alternative prior to trialing food textures during exercises with or without neuromuscular electrical stimulation.

Another therapy method according to the instant invention is to treat oral motor disorders/oral motor weakness. It involves (a) giving chewing gum of a certain resistance or hardness (to be determined by the level of physical deficit/impairment of the patient) to a patient suffering from an oral motor/oral motor weakness; (b) instructing the patient to chew the gum; and (c) depending on the patient's deficits, the patient would use the gum to address those deficits. For example, if the patient has decreased tongue lateralization, the patient would move the gum from side to side laterally in his or her oral cavity. If the patient had weak lip closure, the patient could press the gum between the lips, hold and repeat. Furthermore, if the patient had poor tongue protrusion, the patient could place the therapy gum in between the upper and lower central incisors while protruding the tongue anteriorly through the gum. The result here would be to use the resistance of the gum to strengthen lingual protrusion.

Currently, speech pathologists utilize oral motor exercises to address oral motor deficits, but they are typically performed in isolation without resistance. The therapy gum provides a greater benefit than traditional oral motor exercises because it provides tactile feedback, gustatory stimulation, as well as resistance from the gum. For example, if a patient has poor tongue protrusion, some oral motor exercises involve having the patient protrude their tongue repeatedly for an exercise. In this practice, there is no resistance against the tongue, raising questions as to whether the exercise is truly beneficial. The therapy gum would provide resistance to strengthen the lingual deficit.

The instant method for treating oral motor disorders/oral motor weakness can also be used for the treatment of mild-moderate Trismus (reduced jaw opening). The mastication exercises provided by the therapy gums can address jaw/masseter muscle and temporomandibular joint opening. In this particular therapy, the patient would be instructed to masticate the therapy gum using exaggerated chewing motions to open the jaw wider. Furthermore, because this exercise is conducted in a functional activity (such as mastication, which is used to masticate food), it is believed that exercises performed within functional activities provide greater therapeutic outcomes versus performing an exercise in a non-functional manner to do neuropathway involvement.

SUMMARY AND CONCLUSIONS

What has been provided in the above-described aspects and embodiments of the invention is a group or kit of chewing gums of different hardness or chewing resistance, and a method of using these chewing gums in a chewing therapy session. One would begin by a speech pathologist or other qualified therapist assessing the patient's oral motor function and deciding to utilize an oral mater, mastication, sensory or swallowing exercise program that focuses on mastication such as the proposed invention gum program. A speech pathologist or other qualified therapist would decide what level the patient's impairment was, and choose the appropriate gum resistance level that corresponds to the impairment. The speech pathologist would then have the patient masticate the gum and provide instruction to just masticate, or lateralize the gum from one oral cavity side to the other, or perform other appropriate exercises such as swallowing saliva, maintaining saliva in oral cavity. The speech pathologist may also use the varying hardness gum program for oral stimulation/sensory integration therapy. Depending on the deficit, the gum exercise program could address the impairment through exercise via masticating the gum and/or swallowing the saliva produced by masticating the gum to improve swallowing function. In addition, the article and methods of the instant invention could be used for sensory feedback via the varying degrees of gum hardness itself through mastication and/or via the gustatory stimulation from the lemon and other flavors. Then, the speech pathologist could use one gum of one level of resistance or follow a sequence of resistance from less resistance to higher resistance through choosing the different gum hardnesses, such as starting with items five and finishing with item one. Alternatively, the speech pathologist could use a sequence of higher resistance to less resistance such as commencing the program with item number one and finishing with item number five, depending on the patient's impairments.

The gum exercise program will use the varying gum hardnesses as exercises for the muscles of the mouth. The instant gum exercise program is more functional and similar to masticating real food, for example, by the gustatory response of the lemon and sour flavors, that is, stimulating the taste buds and eliciting saliva production.

An artisan of ordinary skill will appreciate that various modifications may be made to the invention herein described without departing from the scope or spirit of the invention as defined in the appended claims.

What is claimed is:

1. A method for treating oral dysphagia comprising:
   (a) giving chewing gum of a specific hardness grade to a patient suffering from oral dysphagia;
   (b) instructing the patient to chew the chewing gum for an extended period of time; and
   (c) having a therapist perform an evaluation of a chewing performance of the patient, and making a recommendation as to whether or not the patient should progress to a chewing gum of a next hardness grade.

2. The method of claim 1, further comprising:
   (a) providing a kit comprising a plurality of chewing gums of different hardness; and
   (b) having the therapist perform an initial evaluation of the patient, and make an initial recommendation regarding a hardness level of a chewing gum to be provided to the patient.

3. The method of claim 2, wherein said kit comprises at least five chewing gums.

4. The method of claim 2, wherein said kit comprises at least five chewing gums, each of said gums having a different hardness.

5. The method of claim 2, wherein said plurality of chewing gums are color-coded according to hardness.

6. The method of claim 2, wherein a softest gum of said plurality of chewing gums has a hardness of about 8 on the Shore OO durometer scale.

7. The method of claim 2, wherein a hardest gum of said plurality of chewing gums has a hardness of about 58 on the Shore OO durometer scale.

8. The method of claim 1, wherein said instruction further comprises instructing the patient to masticate the chewing gum of a specific hardness grade, then lateralize the chewing gum of a specific hardness grade with the patient's tongue from the affected side and back and forth, and instructing the patient to use a lingual sweep strategy to maneuver the chewing gum of a specific hardness grade from the affected side.

9. The method of claim 1, wherein said oral dysphagia includes a pharyngeal dysphagia, and further wherein said chewing gum of a specific hardness grade also induces salivation, said method further comprising:
   (a) further instructing the patient to begin to chew to produce saliva; and
   (b) when the patient develops enough saliva, having the patient initiate a swallow of the saliva while not swallowing said chewing gum of a specific hardness grade.

10. The method of claim 9, further comprising as part of step (b), having the patient focus on an effortful swallow.

11. The method of claim 9, wherein said chewing gums of a specific hardness grade and a next hardness grade further comprise a component providing a sour taste.

12. The method of claim 11, wherein said sour taste comprises a lemon taste.

13. The method of claim 11, wherein said component providing a sour taste comprises citric acid.

14. The method of claim 9, wherein said chewing gums of a specific hardness grade and a next hardness grade further comprise a component providing a sweet taste.

15. The method of claim 9, wherein said chewing gums of a specific hardness grade and a next hardness grade further comprise a component providing a peppermint taste.

16. The method of claim 1, wherein said instruction further comprises instructing the patient to use the chewing gum of a specific hardness grade to address said oral dysphagia.

17. The method of claim 16, wherein said oral dysphagia comprises decreased tongue lateralization, and said instruction to address said dysphagia comprises having the patient move the chewing gum of a specific hardness grade from side to side (laterally) in the patient's oral cavity.

18. The method of claim 16, wherein said oral dysphagia comprises weak lip closure, and said instruction to address said dysphagia comprises having the patient press the chewing gum of a specific hardness grade between the patient's lips, hold and repeat.

19. The method of claim 16, wherein said oral dysphagia comprises poor tongue protrusion (sticking out of the patient's tongue forward), and said instruction to address said dysphagia comprises having the patient place the chewing gum of a specific hardness grade in between the patient's upper and lower central incisors while protruding the patient's tongue anteriorly through the chewing gum of a specific hardness grade, using a resistance of the chewing gum of a specific hardness grade to strengthen lingual protrusion.

20. The method of claim 16, wherein said oral dysphagia comprises reduced jaw opening, and said instruction to address said dysphagia comprises having the patient masticate the chewing gum of a specific hardness grade using exaggerated chewing motions to open the patient's jaw and temporomandibular joint wider.

* * * * *